US008267968B2

(12) United States Patent
Remington et al.

(10) Patent No.: US 8,267,968 B2
(45) Date of Patent: Sep. 18, 2012

(54) PERCUTANEOUS SYSTEM FOR DYNAMIC SPINAL STABILIZATION

(75) Inventors: Benjamin J. Remington, Modesto, CA (US); Daniel R. Baker, Seattle, WA (US); Keith W. Kirkwood, Bainbridge Island, WA (US)

(73) Assignee: NeuroPro Technologies, Inc., Modesto, CA (US)

( * ) Notice: Subject to any disclaimer, the term of this patent is extended or adjusted under 35 U.S.C. 154(b) by 410 days.

(21) Appl. No.: 12/491,153

(22) Filed: Jun. 24, 2009

(65) Prior Publication Data
US 2010/0331885 A1 Dec. 30, 2010

(51) Int. Cl.
A61B 17/70 (2006.01)
(52) U.S. Cl. ...................................................... 606/264
(58) Field of Classification Search .................. 606/301, 606/246–278
See application file for complete search history.

(56) References Cited

U.S. PATENT DOCUMENTS

| | | | |
|---|---|---|---|
| 5,084,048 A | 1/1992 | Jacob et al. | |
| 5,891,145 A | 4/1999 | Morrison et al. | |
| 6,530,909 B1 | 3/2003 | Nozaki et al. | |
| 6,530,929 B1 * | 3/2003 | Justis et al. | 606/103 |
| 6,616,667 B1 | 9/2003 | Steiger et al. | |
| 6,783,527 B2 | 8/2004 | Drewry et al. | |
| 7,011,660 B2 | 3/2006 | Sherman et al. | |
| 7,073,415 B2 | 7/2006 | Casutt et al. | |
| 7,125,410 B2 | 10/2006 | Freudiger | |
| 7,862,588 B2 * | 1/2011 | Abdou | 606/246 |
| 8,083,776 B2 * | 12/2011 | Alvarez | 606/265 |
| 2004/0215190 A1 * | 10/2004 | Nguyen et al. | 606/61 |
| 2005/0065516 A1 | 3/2005 | Jahng | |
| 2005/0065517 A1 | 3/2005 | Chin | |
| 2005/0131408 A1 | 6/2005 | Sicvol et al. | |
| 2005/0143737 A1 | 6/2005 | Pafford et al. | |
| 2006/0084979 A1 * | 4/2006 | Jackson | 606/61 |
| 2006/0111712 A1 | 5/2006 | Jackson | |
| 2006/0111713 A1 | 5/2006 | Jackson | |
| 2006/0111715 A1 | 5/2006 | Jackson | |
| 2008/0051787 A1 * | 2/2008 | Remington et al. | 606/61 |
| 2009/0118772 A1 * | 5/2009 | Diederich et al. | 606/301 |
| 2009/0264930 A1 * | 10/2009 | Mcbride | 606/250 |
| 2010/0036443 A1 * | 2/2010 | Hutton et al. | 606/86 R |
| 2010/0249856 A1 * | 9/2010 | Iott et al. | 606/86 A |

FOREIGN PATENT DOCUMENTS

| | | |
|---|---|---|
| EP | 0727188 B1 | 11/1998 |
| EP | 0669109 B1 | 5/1999 |
| FR | 2777449 A1 | 10/1999 |

OTHER PUBLICATIONS

DePuySpine Products, "Viper System," http://www.depuyspine.com/products/mis/viper.asp, DePuy Spine, Inc., California (Aug. 15, 2006).
Mueller, Wolfgang "Dynamic Re-Stabilization of Spinal Segments," Sulzer Medica Journal, Ed. Feb. 1998, Sulzer Orthopedics, Ltd., Baar Switzerland.

\* cited by examiner

*Primary Examiner* — Eduardo C Robert
*Assistant Examiner* — James Palmer
(74) *Attorney, Agent, or Firm* — Janet Sleath; Speckman Law Group PLLC

(57) ABSTRACT

Bone anchoring assemblies for use with minimally invasive surgery (MIS) techniques for dynamic stabilization of the spine, together with placement systems for use in such techniques are provided.

4 Claims, 8 Drawing Sheets

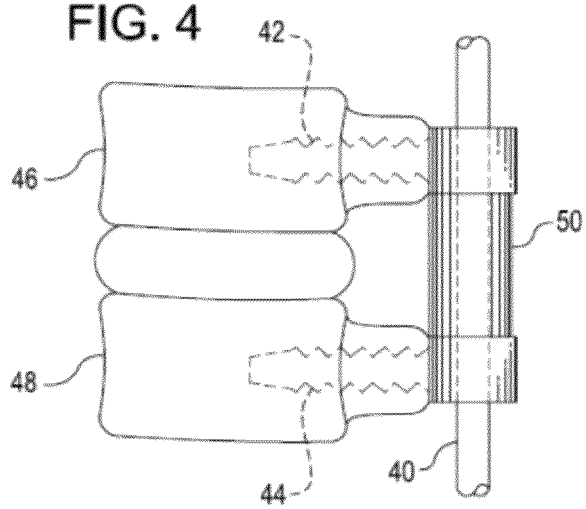
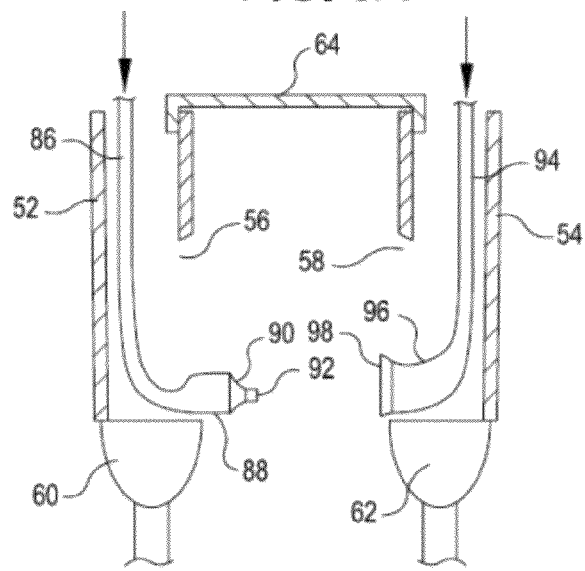
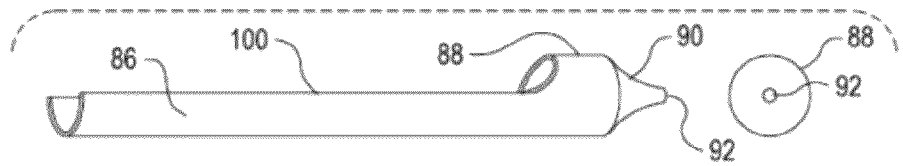
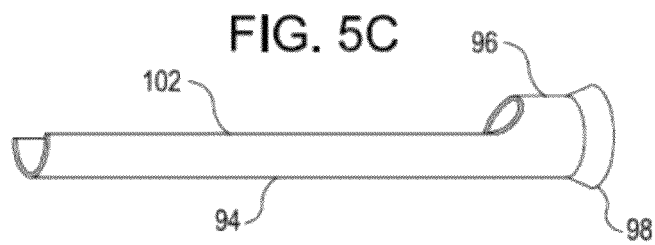

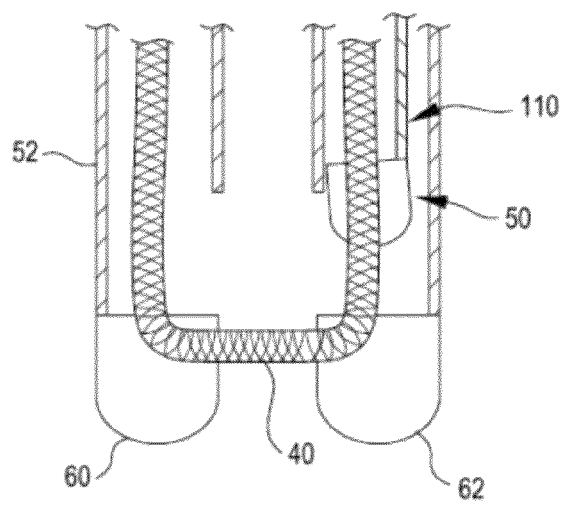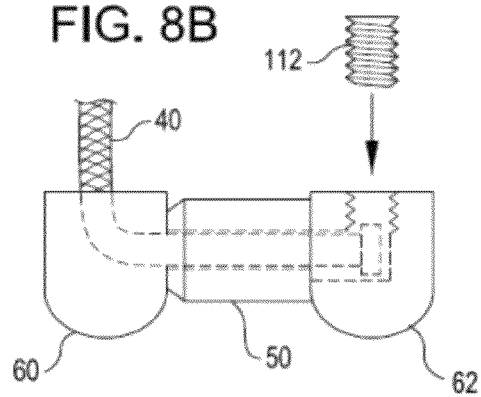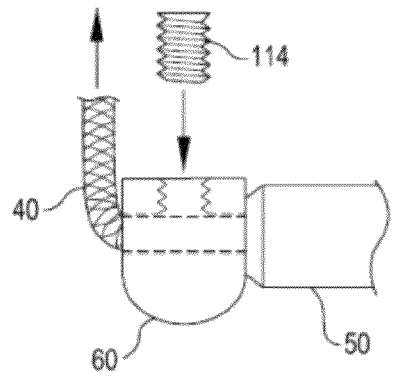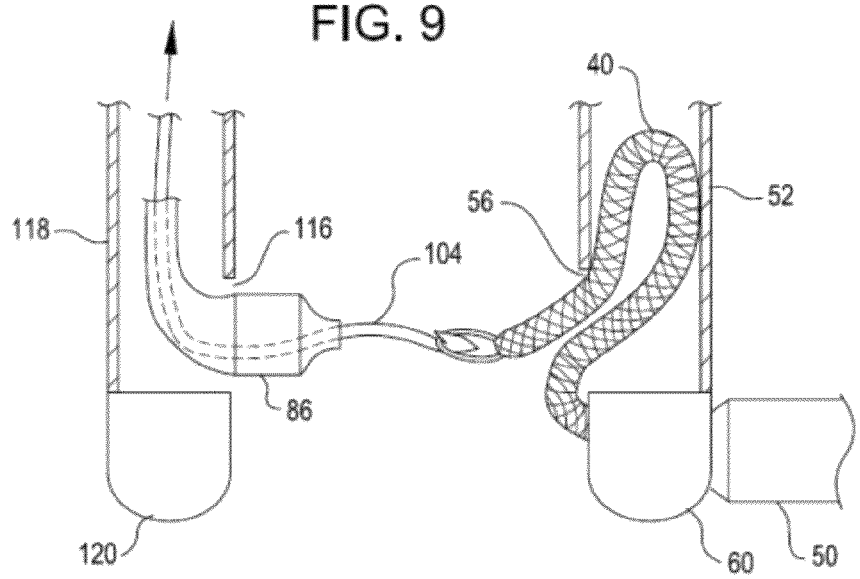

PERCUTANEOUS SYSTEM FOR DYNAMIC SPINAL STABILIZATION

FIELD OF THE INVENTION

The present invention relates generally to methods and systems for the treatment of disorders of the spine, and more specifically to methods and systems for dynamic stabilization of the spine.

BACKGROUND OF THE INVENTION

Lower back pain is one of the most common, and one of the most expensive, disorders afflicting industrialized societies. Conservative treatments include rest, application of ice or heat, exercise, physical therapy, narcotics, steroids and weight control. If these treatments are insufficient to control pain and allow return to normal activity, surgical treatment may be required in which all or part of one or more degenerated, ruptured or otherwise failing discs is removed. This is followed by insertion of an interbody device, for example an artificial disc or fusion implant, and/or fusion of adjacent vertebrae. While fusion surgery is effective in a majority of cases, it has several disadvantages including a reduced range of spinal motion and an increased load transfer to adjacent levels of the spine, which accelerates degeneration at those levels and increases the likelihood of later problems with adjacent spinal segments. External stabilization of spinal segments, either alone or in combination with lumbar fusion and/or implantation of interbody devices, provides significant advantages over lumbar fusion alone, including prevention or reduction of pain.

U.S. Pat. No. 6,530,929 describes instruments for use in placing a brace, or stabilization device, in for example the spine. The brace comprises at least two anchors, such as pedicle screws, that are placed in adjacent vertebrae and a generally rigid rod that extends between, and is held in place by, the two pedicle screws. This spinal stabilization system, known as the Sextant™ system, is commercially available from Medtronic, Inc. (Minneapolis, Minn.). The Sextant™ system, which employs multiaxial pedicle screw implants and pre-contoured rods that are inserted percutaneously, requires the surgeon to make three, relatively small, incisions in order to place two pedicle screws and the rod—one to insert each of the screws and one to insert the rod.

A similar system, known as the Viper™ System, is available from DePuySpine, Inc. (Raynham, Mass.). While the Viper™ system also employs pedicle screws and a generally rigid rod, it only requires the surgeon to make two incisions—one to insert each screw. This is achieved by introducing the rod through a closed screw extension using a rod holder that is rotated through 90°. While systems such as the Viper™ and the Sextant™ systems can be employed to stabilize the spine, they have the disadvantage of preventing any motion between the two adjacent vertebrae.

In order to overcome this problem, dynamic stabilization systems have been designed that are intended to stabilize the spine by controlling abnormal spinal motion while preserving near normal spine function. US Patent Publication No. 2005/0143737 describes a stabilization system that employs at least one flexible element interposed between a bone anchor, such as a pedicle screw, and a generally rigid stabilization member, such as a rod or plate. Such a system, which would be difficult to implement in practice, is not yet commercially available.

The Dynesys™ system from Zimmer, Inc. (Warsaw, Ind.) is a dynamic stabilization system that is designed to bring lumbar vertebrae back into a more natural anatomical position while stabilizing affected spinal segments. This system, which is described for example in U.S. Pat. No. 7,073,415 and European Patent EP0669109B1, the disclosures of which are hereby incorporated by reference, is designed to be used either as a stand-alone treatment or in conjunction with fusion surgery. The system includes at least two pedicle screws that are anchored in adjacent vertebrae, and a flexible stabilizing cord that is threaded through, and extends between, the pedicle screws. The stabilizing cord consists of functional, working and inserting zones having varying thickness and flexibility. A separating cushion, or spacer, through which the cord passes, is positioned between the two pedicle screws. The stabilizing cord limits bending movements while the spacer holds the spinal segments in an anatomically functional position.

The Dynesys™ system is implanted by exposing the back of the spinal segment, inserting the pedicle screws into the vertebrae, cutting the spacers to the correct size, and putting the stabilizing cord in place. When employed to stabilize more than one spinal segment, the spacers are inserted segment by segment. The stabilizing cord is fixed in the eyes of the pedicle screws by mean of set screws. The surgeon can pretension the stabilizing cord separately for each spinal segment before fixing the cord in the pedicle screws, using a specially designed instrument. The stabilizing cord is then cut to the required length and the wound is closed. The main disadvantage of the Dynesys™ system is that significant spinal exposure and paraspinous muscle stripping is necessary in order to place the hardware, requiring the surgeon to make a relatively large incision. This leads to increased trauma with an associated increase in recovery time and risk of complications. In addition, the instrumentation for the Dynesys™ system is clumsy and does not permit a percutaneous approach.

US Patent Publication No. 2005/0065516 discloses a spinal fixation device comprising two securing members, such as pedicle screws, and a flexible metal connection unit connected to the two securing members, wherein the metal connection unit comprises a metal tube or pipe. In certain embodiments, the outer surface of the metal tube is provided with spiral cuts or grooves to provide a desired level of flexibility.

Many commercially available systems for spinal stabilization employ polyaxial screws, as described, for example, in U.S. Pat. No. 5,891,145. Polyaxial screws comprise a bone engaging portion, or fastener, and a head portion that may be positioned at any of a continuous range of angles relative to the bone engaging portion, thereby allowing a surgeon some flexibility in positioning the screw in the vertebrae. However, polyaxial screws are limited in terms of the amount of force that can be applied to them compared to fixed-head screws, as slippage between the head portion and the bone engaging portion tends to occur at forces greater than 200-300 Newtons.

There remains a need for an effective dynamic spinal stabilization system that can be implanted in a patient using minimally invasive procedures.

SUMMARY OF THE INVENTION

The present invention provides bone anchoring assemblies for use with minimally invasive surgery (MIS) techniques for dynamic stabilization of the spine, together with placement systems for use in such techniques. The bone anchoring assemblies and placement systems disclosed herein may be effectively employed in the treatment of acute and chronic instabilities or deformities of the vertebral spine, including the thoracic, lumbar, sacral and/or cervical spine, such as, but not limited to, degenerative disc diseases, spinal stenosis, spondylolithesis, spinal deformities (for example, degenerative scoliosis, kyphosis and/or lodosis), fractures and dislocations due to physical trauma, pseudarthrosis and tumor resection. The disclosed assemblies and systems may be used in conjunction with techniques such as fusion treatments, in which a surgeon removes portions of the affected disc and bone from the spine.

Use of minimally invasive systems allows a surgeon to effectively stabilize two or more adjacent vertebrae, while maintaining some degree of motion, without making large incisions. This reduces the amount of trauma to the patient and decreases the recovery time. Using the placement system disclosed herein, the surgeon need only make a small number of small incisions, for example two, on each side of the spine, to give a total of four incisions, when stabilizing two adjacent vertebrae. Furthermore, each incision need only be a stab incision of about 7-10 mm in length.

The disclosed bone anchoring assemblies and placement systems may be employed with various systems for spinal stabilization, including, but not limited to, the system described in US Patent Publication No. 2008/0051787, the disclosure of which is hereby incorporated by reference.

In certain embodiments, a bone anchoring assembly is provided that comprises (a) a bone engaging member, the bone engaging member comprising a shank portion and a head portion located at a proximal end of the shank portion; (b) a receiving member that is sized to receive and retain the head portion; and (c) a retaining member that is sized to be positioned in the receiving member and engage the head portion. The head portion is provided with a first mating configuration that engages a second mating configuration provided on a distal region of the receiving member, the first and second mating configurations being shaped and sized to permit orientation of the receiving member at any one of a series of discrete, pre-determined angles relative to the bone engaging member, whereby the receiving member may be retained in position at a desired angle. In one embodiment, the first and second mating configurations interdigitate with each other. The first mating configuration may comprise a plurality of circumferential shoulders, with the diameter of each shoulder being smaller than that of a proximally adjacent shoulder and the second mating configuration comprises a plurality of circumferential notches that engage, and interdigitate with, the plurality of circumferential shoulders.

In other embodiments, methods for transferring an elongated stabilization member percutaneously between a first pedicle screw and a second pedicle screw are provided. Such methods comprise (a) attaching a first guide tube and a second guide tube to head portions of the first and second pedicle screws, respectively, each of the first and second guide tubes having an aperture in a distal region and the guide tubes being positioned with the apertures facing each other; (b) inserting a hollow elongated guide element introducer at a proximal end of the first guide tube and advancing the guide element introducer until the distal end of the guide element introducer extends out of the aperture of the first guide tube and towards the aperture second guide tube, wherein the distal end of the guide element introducer has a reduced diameter tip provided with an aperture; and (c) inserting a hollow elongated guide element receiver at a proximal end of the second guide tube and advancing the guide element receiver until the distal end of the guide element receiver extends out of the aperture of the second guide tube and towards the first guide tube, wherein the distal end of the guide element receiver has an increased diameter tip provided with an aperture. A guide element is introduced into a proximal end of the guide element introducer and advanced out through the aperture in the reduced diameter tip, into the aperture of the increased diameter tip of the guide element receiver, and through the guide element receiver until a tip of the guide element exits the proximal end of the guide element receiver. One end of the stabilization member is then attached to the tip of the guide element, and the guide element and the stabilization member are withdrawn back through the guide element receiver and the guide element introducer. The guide element introducer and guide element receiver are subsequently removed from the first and second guide tubes, and the stabilization member is anchored in the head portions of the first and second pedicle screws using techniques well know to those of skill in the art.

A clamping mechanism may be attached to the proximal ends of the first and second guide tubes in order to maintain the orientation of the first and second guide tubes with respect to each other as detailed below. At least one of the guide element introducer and the guide element receiver may be provided with a region of increased flexibility in proximity to its distal end.

In other embodiments, systems for use in such methods are provided, the systems comprising: (a) a first guide tube and a second guide tube sized and shaped to engage head portions of the first and second pedicle screws, respectively, each of the first and second guide tubes having an aperture in a distal region; (b) a hollow elongated guide element introducer sized to be received in and extend through the first guide tube, wherein the distal end of the guide element introducer has a reduced diameter tip having an aperture through which a guide element may be extended; and (c) a hollow elongated guide element receiver sized to be received in and extend through the second guide tube, wherein the distal end of the guide element receiver has an increased diameter tip having an aperture through which a guide element may be inserted.

These and additional features of the present invention and the manner of obtaining them will become apparent, and the invention will be best understood, by reference to the following more detailed description and the accompanying drawings.

BRIEF DESCRIPTION OF THE DRAWINGS

The present invention will be described in greater detail in the following detailed description, with reference to the accompanying drawings, wherein:

FIG. 4 illustrates a dynamic stabilization system implanted in a spinal segment.

FIG. 5A illustrates one embodiment of a placement system for introducing a dynamic stabilization system in a spinal segment, the placement system comprising first and second guide tubes, a guidewire introducer and a guidewire receiver, with FIGS. 5B and 5C illustrating the guide wire introducer and guidewire receiver, respectively.

FIGS. 8A-C illustrate the positioning of a spacer on the stabilization cord and engagement of the cord in the head portions of two pedicle screws using the system of FIG. 5A.

FIG. 9 illustrates the use of the system of FIG. 5A to position the stabilization cord in the head portion of a third pedicle screw.

DETAILED DESCRIPTION OF THE INVENTION

Figure 1:
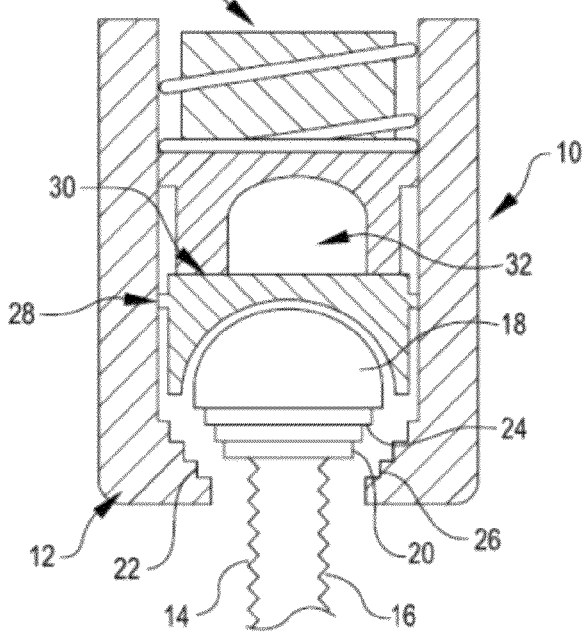
FIG. 1 is a side view of a bone anchoring assembly disclosed herein comprising a receiving member and a bone engaging member.

In one embodiment, illustrated in FIGS. 1 and 2A-C, a bone anchoring assembly 10 is provided that comprises a receiving member 12 that is configured to receive and retain a spinal stabilization member, such as a rod or cord, to be extended between two or more vertebrae, together with a bone engaging member 14. Bone engaging member 14 comprises a generally elongated shank portion 16 and an enlarged head portion 18 located at a proximal end of shank portion 16. Shank portion 16 generally tapers towards its distal end and may be threaded to facilitate engagement in a bone, such as a vertebra. In the embodiment illustrated herein, shank portion 16 is threaded, however those of skill in the art will appreciate that other designs of shank portions may be effectively employed in the systems disclosed herein. Receiving member 12 is sized to receive and movably retain enlarged head portion 18 of bone engaging member 14 and may, for example, be tulip-shaped. Enlarged head portion 18 is provided with a first mating configuration 20 that engages a second mating configuration 22 provided in a distal region of receiving member 12 whereby receiving member 12 may be oriented and retained at any one of a series of discrete, pre-determined angles relative to bone engaging member 14. In one embodiment, first mating configuration 20 comprises a plurality of circumferential shoulders 24, with the diameter of each shoulder being smaller than that of the proximally adjacent shoulder. Second mating configuration 22 comprises a plurality of circumferential notches 26 that engage, and interdigitate with, circumferential shoulders 24 provided on enlarged head portion 18. Shoulders 24 and/or notches 26 may be circumferentially continuous or discontinuous. For example, in the embodiment illustrated in FIGS. 3A-C, receiving member 12 is provided with a plurality of discontinuous notches 26 which are able to engage circumferential shoulders on enlarged head portion 18.

Figure 2A:
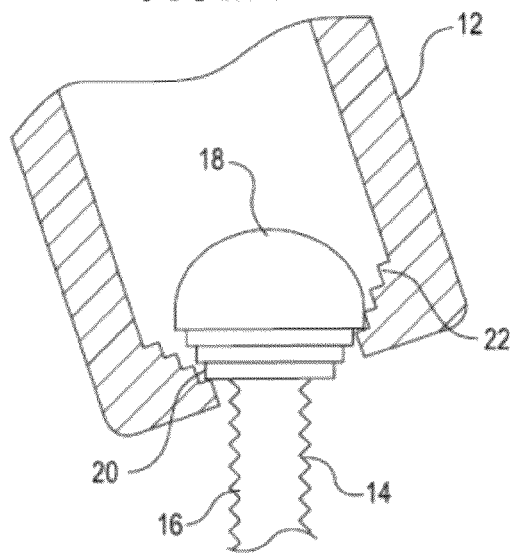
FIG. 2A is a side view of the bone anchoring assembly of FIG. 1 with the receiving member fixed at a desired angle relative to the bone engaging member, with FIG. 2B illustrating the head portion of the bone engaging member, and FIG. 2C illustrating the receiving member.
Figure 2B:
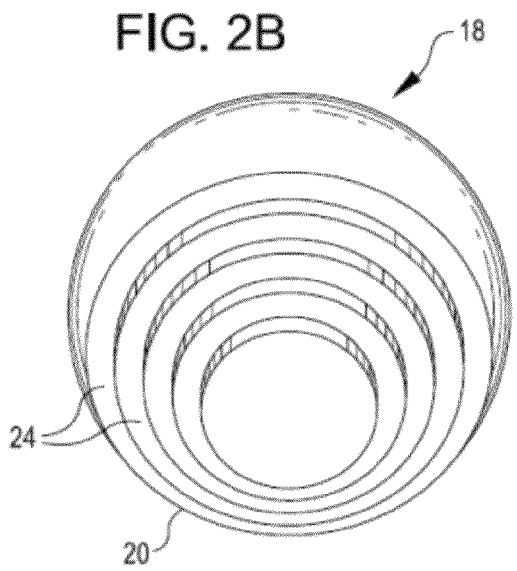
Figure 2C:
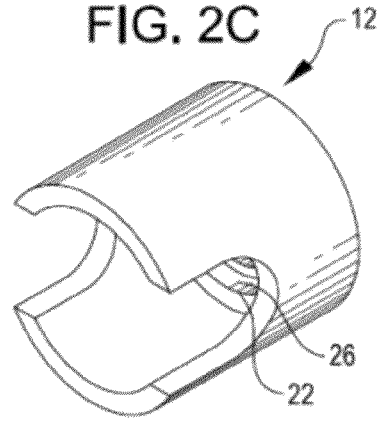
Figure 3A:
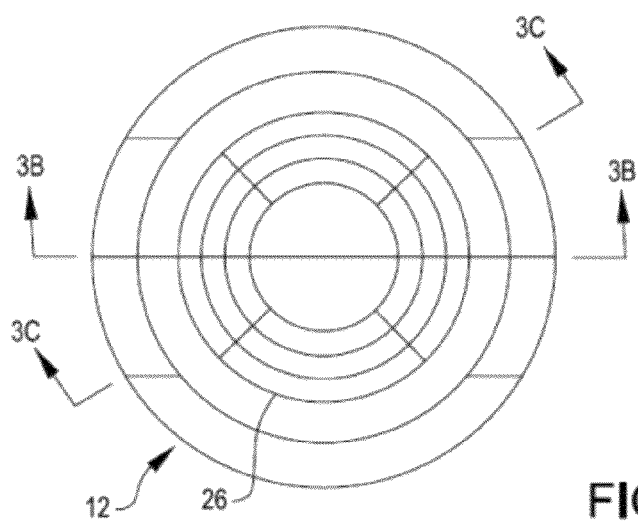
FIG. 3A is a top view of a receiving member having discontinuous notches, or steps, with FIGS. 3B and 3C being cross-sections of the receiving member of FIG. 3A along lines B-B and C-C, respectively.
Figure 3B:
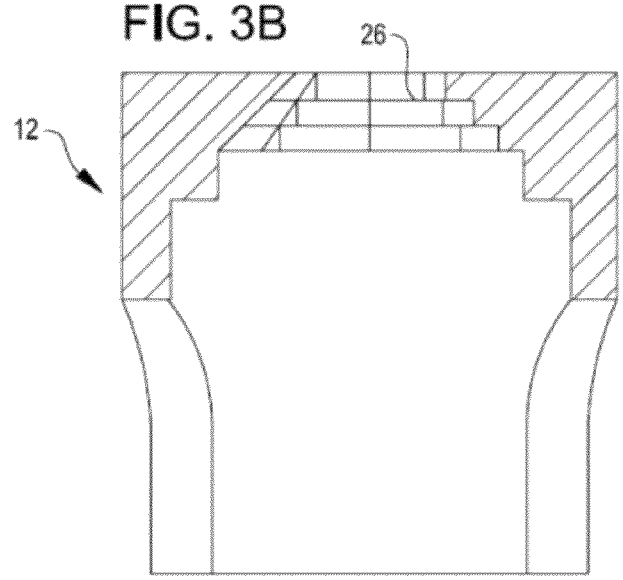
Figure 3C:
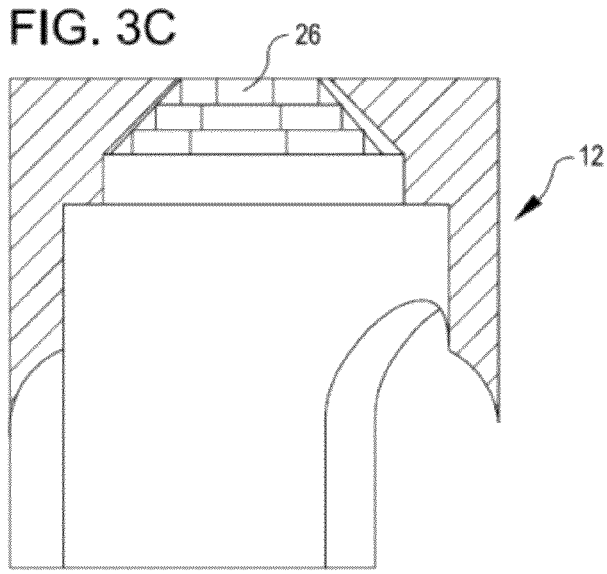

In use, enlarged head portion 18 of bone engaging member 14 is positioned in receiving member 12 such that shank portion 16 of bone engaging member 14 extends out of the distal end of receiving member 12. Shank portion 16 is then inserted into a bone, such as a vertebra, using known methods, and receiving member 12 is positioned at one of a number of predetermined discrete angles, such as, but not limited to, 5°, 10° or 15°, relative to shank portion 16 of bone engaging member 14, as shown in FIG. 2A. A screw retaining member 28, such as a screw head-conforming washer, is positioned in receiving member 12 and engages enlarged head portion 18, thereby locking receiving member 12 in place at the desired angle. The elongated member, such as a cord, is then positioned in receiving member 12 and retained therein. In one embodiment, the cord is retained in receiving member 12 by means of a cord retaining member 30 having a passage 32 extending there through that is sized to receive the cord. Cord retaining member 30 and passage 32 are sized and shaped such that, once cord retaining member is positioned on retaining member 28, the cord is compressed sufficiently for it to be securely retained but cannot be over-compressed, thereby avoiding accidental damage to the cord.

Cord retaining member 30 is held in position by means of a locking cap 34, such as a set screw having threads that engage corresponding threads on receiving member 12. Alternative methods for holding an elongated member, such as a rod or cord, in receiving member 12 are well known to those of skill in the art and may be effectively employed with the disclosed bone anchoring assembly. For example, locking cap 34 may be provided with two protrusions positioned on opposing sides of locking cap 34 which engage notches, or slots, provided on inner surfaces of receiving member 12.

Receiving member 12 and bone engaging member 14 of bone anchoring assembly 10 are formed of a durable, generally rigid, biocompatible material, such as, but not limited to, carbon fiber, titanium, titanium alloys, Nitinol™, cobalt-chromium alloys and cobalt-chromium-molybdenum alloys. Bone engaging member 14 may be cannulated in order to allow use of a guidewire for positioning the bone anchoring assembly.

Using the disclosed bone anchoring assembly, significantly higher forces may be employed compared to known polyaxial pedicle screws. This is due to the interdigitation of surfaces employed in the disclosed assembly, which permits the application of greater forces than can be applied using prior polyaxial screws which only employ friction. As will be appreciated by those skilled in the art, bone anchoring assembly 10 and/or regions thereof may be radiopaque or may be provided with one or more radiopaque markers, in order to facilitate positioning of the assembly by a surgeon.

The bone anchoring assembly disclosed herein may be employed in minimally invasive systems for spinal stabilization, including a dynamic stabilization system as described below. FIG. 4 illustrates a dynamic stabilization system implanted in a spinal segment, the system comprising a flexible elongated spinal stabilization member. The elongated spinal stabilization member, such as a cord 40, extends between and is retained by two pedicle screws 42 and 44, which are anchored in vertebrae 46 and 48, respectively, using means well known to those of skill in the art. A generally cylindrical spacer 50 is positioned on cord 40 between head portions of pedicle screws 42 and 44. Cord 40 and spacer 50 act to limit movement of vertebrae 46 and 48 relative to each other. Such a dynamic stabilization system is described in detail in US Patent Publication No. 2008/0051787, the disclosure of which is hereby incorporated by reference.

In other embodiments, the present disclosure provides placement systems that may be employed to position such a dynamic stabilization system. In the embodiment illustrated in FIG. 5A, the placement system comprises a first guide tube 52 and a second guide tube 54. Guide tubes 52 and 54, which are generally cylindrical in shape, are open at both distal and proximal ends and are constructed of materials currently employed in similar surgical instruments, such as surgical stainless steel. Each guide tube 52 and 54 is each provided with an aperture 56 and 58 at its lower or distal region. In use, the lower, or distal ends, of guide tubes 52 and 54 are attached to head portions 60 and 62 of pedicle screws 42 and 44, respectively, using means well known in the art, such as notches or screw threads. Head portions 60 and 62 of screws 42 and 44 are generally tulip-shaped and are each provided with a generally U-shaped slot, or recess, that extends through the head portion and is sized to receive and hold a portion of cord 40. Guide tubes 52 and 54 are positioned so that they are as parallel to each other as possible with apertures 56 and 58 facing each other, and may then be connected by means of clamp 64. Clamp 64 is attached to guide tubes 52 and 54 at, or in proximity to, their proximal regions and limits movement of the guide tubes with respect to each other, thereby maintaining the correct position and orientation of guide tubes 52 and 54.

Figure 6A:
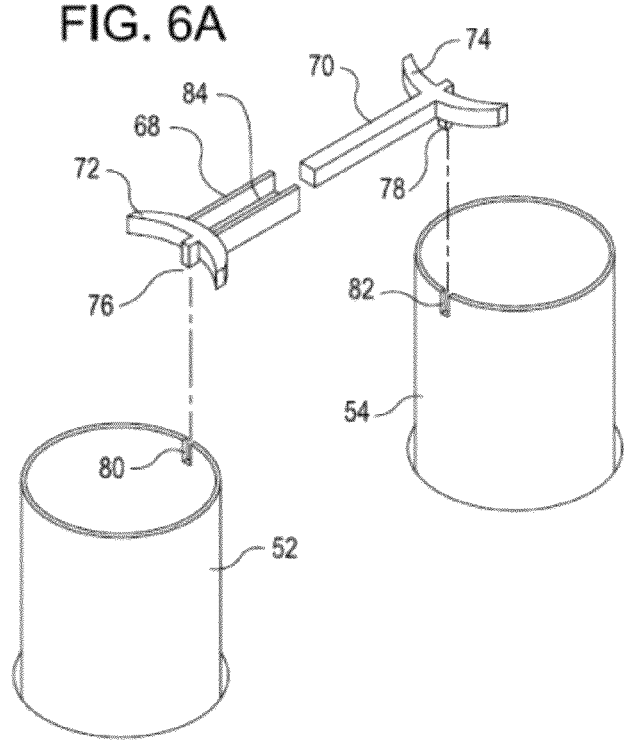
FIGS. 6A-C illustrate a clamping system for holding two guide tubes at a fixed position relative to each other.
Figure 6B:
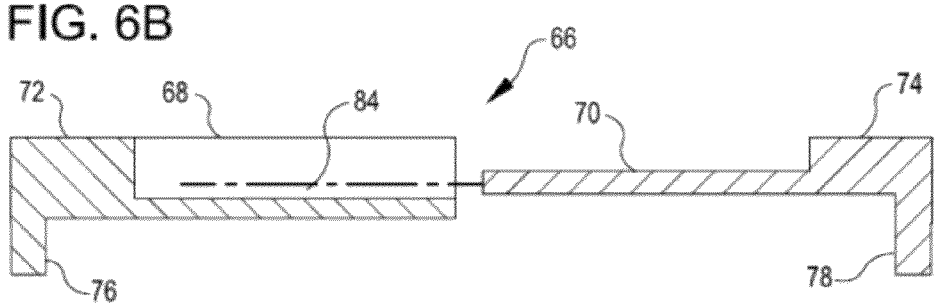
Figure 6C:
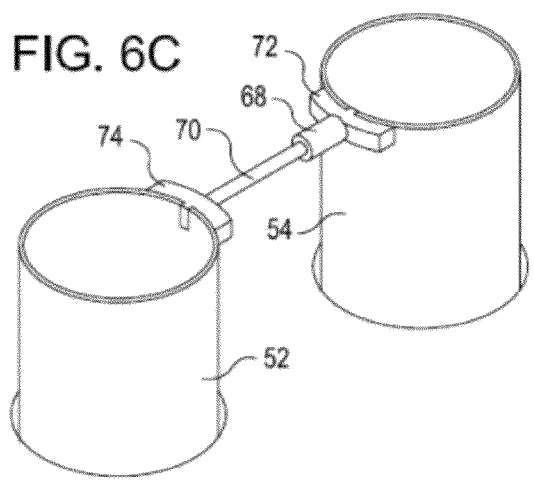
Figure 7A:
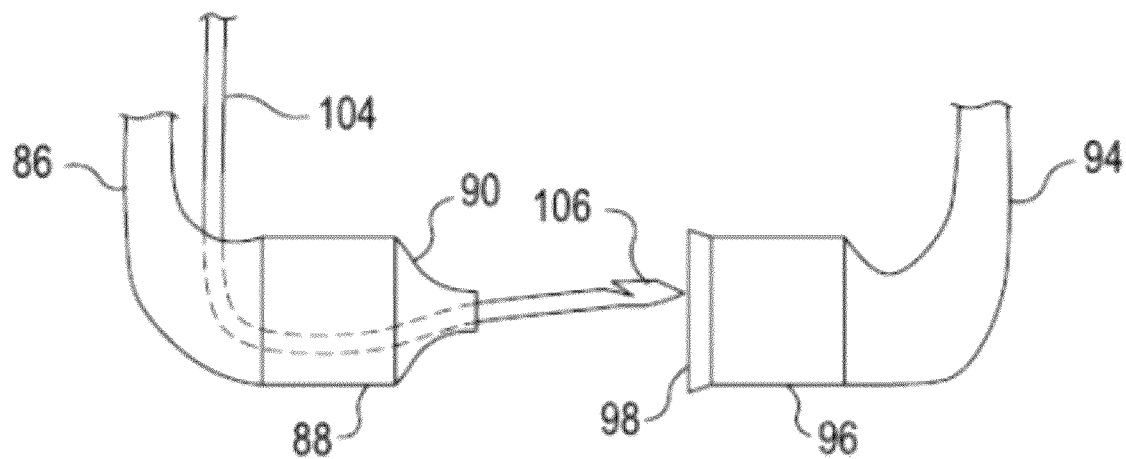
FIGS. 7A and 7B illustrate the insertion of a guidewire in the placement system of FIG. 5A and attachment of the guidewire to a stabilization cord.
Figure 7B:
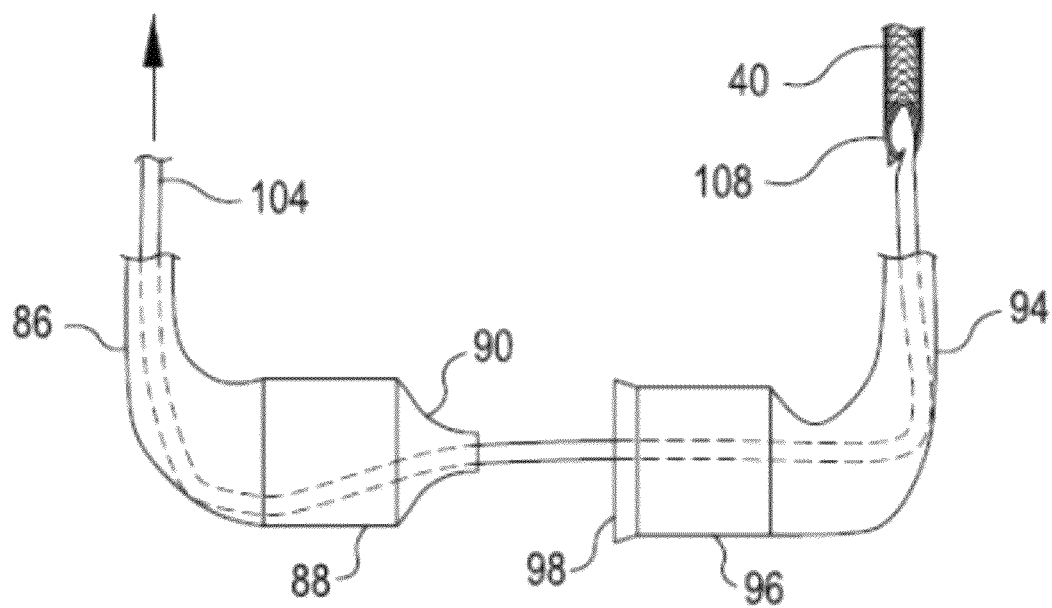

In one embodiment, illustrated in FIGS. 6A-C, the proximal ends of guide tubes 52 and 54 are connected using a clamping system 66 that maintains the proximal ends of guide tubes 52 and 54 in position relative to each other. Clamping system 66 comprises a first elongated portion 68 and a second elongated portion, or rod, 70, each of which is attached to and extends from a engagement portion 72 and 74, respectively. Tube engagement portions 72 and 74 are sized to match and engage an outer surface of guide tubes 52 and 54, respectively, and may, for example, have a generally semi-circular configuration. Tube engagement portions 72 and 74 are held in place on the outer surfaces of guide tubes by means, for example, of protrusions 76 and 78 which are received in notches 80 and 82 provided on a proximal rim of guide tubes 52 and 54, respectively. First elongated portion 68 comprises an elongated trough 84 that is sized to receive and retain second elongated portion, or rod, 70. A scale may be provided adjacent to trough 84 to assist the surgeon in determining the distance between guide tubes 52 and 54 and therefore the distance between pedicle screw head portions 60 and 62.

Returning to FIG. 5A, an elongated guide element introducer 86 is introduced at the proximal end of first guide tube 52 and moved through guide tube 52 until a distal portion 88 of introducer 86 extends out of opening 56 towards second guide tube 54. Distal portion 88 of guide element introducer 86 is provided with a reduced diameter tip 90 having an aperture 92. An elongated guide element receiver 94 is introduced at the proximal end of second guide tube 54 and moved through guide tube 54 until a distal portion 96 of receiver 94 extends out of opening 58 and towards first guide tube 52. Distal portion 96 of guide element receiver 94 is provided with an open-ended increased diameter, or flared, tip 98. The diameter of tip 98 is selected such that a guide element, such as a guide wire, 104 extending out of aperture 92 of reduced diameter tip 90 will be received in increased diameter tip 98. Preferably, increased diameter tip 98 is sized such that guide wire 104 extending from reduced diameter tip 90 will enter increased diameter tip 98 when tips 90 and 98 are separated by a distance of up to 40 mm.

Guide element introducer 86 and guide element receiver 94 are formed of a durable, flexible material, biocompatible material, such as Nitinol. In one embodiment, guide element introducer 86 and guide element receiver 94 may each be provided with a region of increased flexibility 100 and 102 proximal to distal portions 88 and 96, respectively, to facilitate the movement of distal portions 88 and 96 out of openings 56 and 58. As shown in FIGS. 5B and 5C, regions 100 and 102 may be in the form of cut tubes. Other structures that may be employed to increase the flexibility of regions 100 and 102 include, for example, accordion-type tubing.

In use, guidewire 104 is introduced into the proximal end of guide element introducer 86 and advanced distally through aperture 92 in reduced diameter tip 90 and into the open end of increased diameter tip 98 of guide element receiver 94. Advancement of guidewire 40 continues until guidewire tip 106 exits the proximal end of guide element receiver 94. Guidewire tip 106 is then attached to a first end of cord 40 using a connection mechanism. In the illustrated example, guidewire tip 106 is hooked and engages a ring 108 provided on the first end of cord 40. Those of skill in the art will appreciate that guidewire tip 106 may be provided with an alternative configuration and that other connection mechanisms may be employed to attach guidewire tip 106 to cord 40. It will also be understood that the attachment of cord 40 to guidewire 104 may take place inside guide element receiver 94.

Guidewire tip 106 is then retracted by pulling guidewire 104 and guide element introducer 86 back through first guide tube 52 in a proximal direction, thereby pulling the first end of attached cord 40 into first guide tube 52 and positioning cord 40 in head portions 60 and 62 of pedicle screws 42 and 44. Guidewire 104 is detached from cord 40, and guide element introducer 86 and guide element receiver 94 are removed. Spacer 50 threaded onto cord 40 and pushed through second guide tube 54 using pusher 110 until it is in the desired position between pedicle screw head portions 60 and 62 (FIG. 8A). Cord 40 is anchored in first pedicle screw head portion 62 by means, for example, of a first set screw 112, tensioned using techniques well known to those of skill in the art, and anchored in pedicle screw head portion 60 using, for example, a second set screw 114 (FIGS. 8B-C; guide tubes not shown for clarity).

When stabilization of three or more adjacent vertebrae is desired, first guide tube 52 is rotated until opening 56 is facing an opening 116 provided at the distal end of a third guide tube 118 mounted on a third pedicle screw head portion 120 as shown in FIG. 9. Guide element introducer 86 is placed in third guide tube 118 and guidewire 104 is reattached to the first end of cord 40 using guide element receiver 96 essentially as described above. Guidewire 104 and the first end of cord 40 are then pulled down through first guide tube 52 and up through third guide tube 118, and cord 40 is tensioned and secured in third pedicle screw head portion 120 as described above. This procedure can be repeated for additional vertebrae as desired, with cord 40 being cut using known methods following positioning between all the desired vertebrae.

Figure 10A:
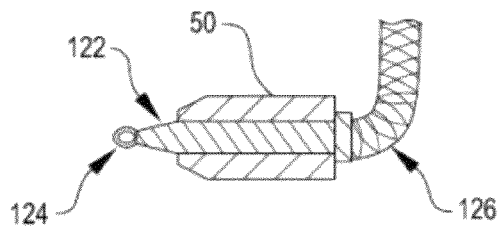
FIGS. 10A-C illustrate an alternative method of positioning a spacer and a stabilization cord between the head portions of two pedicle screws using the system of FIG. 5A.
Figure 10B:
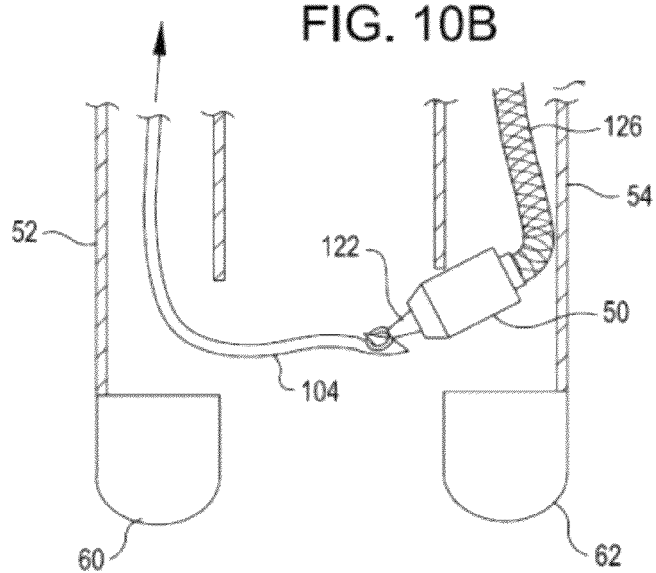
Figure 10C:
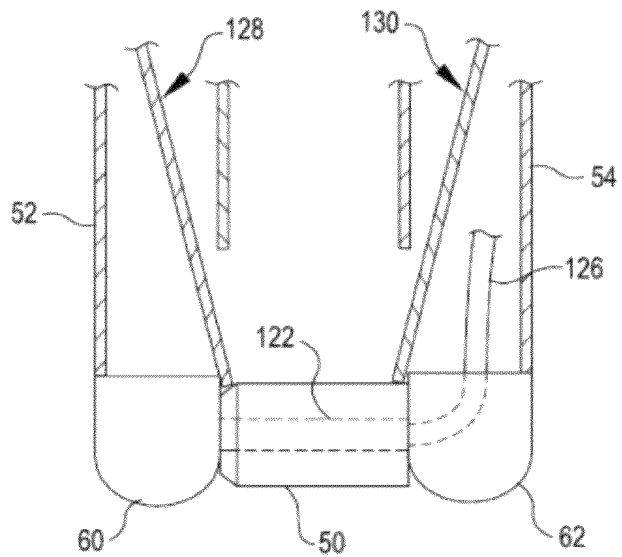

In an alternative embodiment, spacer 50 is positioned between pedicle screw head portions 60 and 62 prior to positioning of cord 40. In this embodiment, spacer 50 is threaded onto a spacer insert 122 having an attachment mechanism, such as a loop or ring, 124 at one end, as shown in FIG. 10A. The other end of spacer insert 122 is attached to an insert retrieval cord or wire, 126. Using first and second guide tubes 52 and 54, guide element introducer 86 and guide element receiver 94 essentially as described above, tip 106 of guidewire 104 is attached to attachment mechanism 124 and spacer 50 is pulled down through second guide tube 54 until it is positioned between first and second pedicle screw head portions 60 and 62, as shown in FIG. 10B (guide element introducer and guide element receiver omitted for clarity). First and second spacer pushers 128 and 130 may be employed to correctly position spacer 50.

When stabilizing three or more vertebrae, this procedure may be repeated to position additional spacers between the vertebrae. Once all the desired spacers have been positioned, cord 40 is either pushed or pulled through the spacers and pedicle screw head portions, tensioned and then cut using means well known to those of skill in the art, such as a guillotine-type cutter.

Figure 11A:
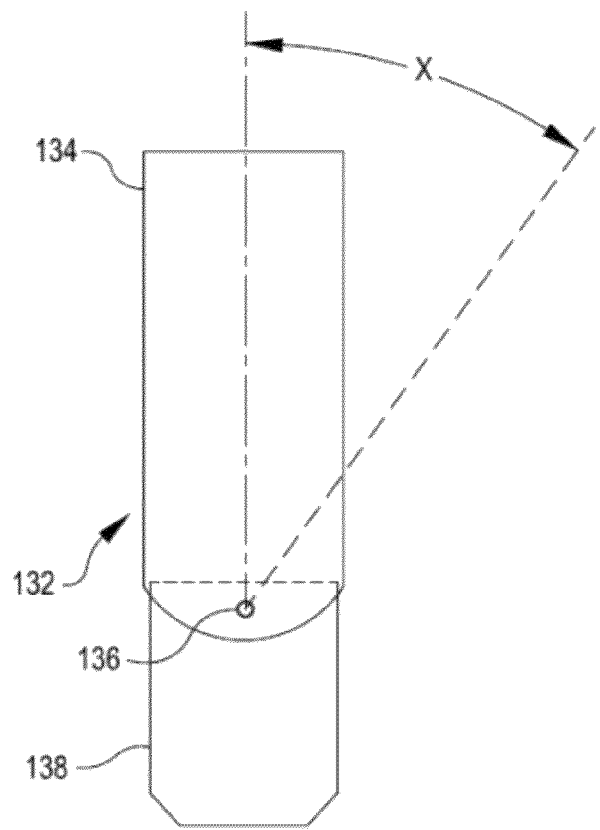
FIGS. 11A and B illustrate an alternative guide tube for use in the disclosed methods.
Figure 11B:
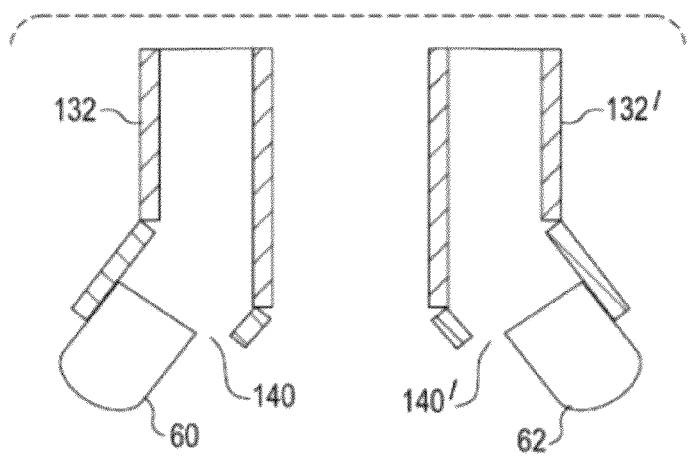

In yet a further embodiment, one or more guide tubes are employed in which the top, or proximal end of each tube is able to flex relative to the bottom, or distal end, of the tube. As illustrated in FIGS. 11A and B, guide tube 132 is provided with a proximal portion 134 that is able to pivot about point 136 with respect to distal portion 138. Proximal portion 134 may, for example, be able to pivot at an angle X of 10-30° with respect to distal portion 138. As can be seen in FIG. 11B, this type of guide tube is particularly useful in situations where pedicle screw head portions 60 and 62 are not aligned due to the orientation of the vertebrae, such as in the L4 and L5 region. As with guide tubes 52 and 54 discussed above, guide tubes 132 and 132' may be provided with openings 140 and 140' through which a guide element introducer and a guide element receiver may extend.

While the present invention has been described with reference to specific embodiments thereof, it should be understood by those skilled in the art that various changes may be made and equivalents may be substituted without departing from the true spirit and scope of the invention. In addition, many modifications may be made to adapt a particular situation, material, composition of matter, method, method step or steps, for use in practicing the present invention. All such modifications are intended to be within the scope of the claims.

All of the publications, patent applications, and patents cited in this application are herein incorporated by reference in their entirety to the same extent as if each individual publication, patent application or patent was specifically and individually indicated to be incorporated by reference in its entirety.

We claim:

1. A system for transferring an elongated stabilization member percutaneously between a first pedicle screw and a second pedicle screw, comprising:

(a) a first guide tube and a second guide tube sized and shaped to engage head portions of the first and second pedicle screws, respectively, each of the first and second guide tubes having an aperture in a distal region;

(b) a hollow elongated guide element introducer sized to be received in and extend through the first guide tube, wherein the distal end of the guide element introducer has a reduced diameter tip having an aperture through which a guide element may be extended; and (c) a hollow elongated guide element receiver sized to be received in and extend through the second guide tube, wherein the distal end of the guide element receiver has an increased diameter tip having an aperture through which a guide element may be inserted; and (d) a clamping mechanism sized and shaped to retain the proximal ends of the first and second guide tubes in order to maintain the orientation of the first and second guide tubes with respect to each other.

2. The system of claim 1, wherein at least one of the guide element introducer and the guide element receiver is provided with a region of increased flexibility in proximity to its distal end.

3. The system of claim 1, wherein the guide element introducer and the guide element receiver are formed of a flexible material.

4. The system of claim 3, wherein the flexible material is Nitinol.

* * * * *